United States Patent [19]
Hasson

[11] Patent Number: 5,601,577
[45] Date of Patent: Feb. 11, 1997

[54] APPARATUS FOR ASSISTING THE TYING OF A SUTURE

[76] Inventor: Harrith M. Hasson, 2551 N. Clark St., 9th Fl., Chicago, Ill. 60614

[21] Appl. No.: 328,879

[22] Filed: Oct. 25, 1994

[51] Int. Cl.⁶ ................................................. A61B 17/00
[52] U.S. Cl. .......................................... 606/148; 606/139
[58] Field of Search ................................. 606/139, 144, 606/148; 289/17

[56] References Cited

U.S. PATENT DOCUMENTS

| | | | |
|---|---|---|---|
| 1,816,952 | 8/1931 | Bergman | 606/139 |
| 4,641,652 | 2/1987 | Hutterer et al. | 606/148 |
| 5,087,263 | 2/1992 | Li | 606/148 |
| 5,364,409 | 11/1994 | Kuwabara et al. | 606/148 |
| 5,454,821 | 10/1995 | Harm et al. | 606/148 |

FOREIGN PATENT DOCUMENTS 0759388  10/1956  United Kingdom ................... 606/144

*Primary Examiner*—Jeffrey A. Schmidt
*Attorney, Agent, or Firm*—Wood, Phillips, VanSanten, Clark & Mortimer

[57] ABSTRACT

An instrument for facilitating the formation of a knot in a flexible line having a first portion extending through a tissue/organ and first and second free ends projecting away from the first portion. The instrument has a body defining a passage through which the first and second free ends of the flexible line can be passed in a first direction to be exposed at a tying location on the body. First structure is provided on the body for supporting a suture loop defined by wrapping the first and second free ends of the flexible line around each other. Second structure is provided on the body, spaced from the first structure, for releasably holding one of the first and second free ends of the flexible line.

17 Claims, 2 Drawing Sheets

APPARATUS FOR ASSISTING THE TYING OF A SUTURE

BACKGROUND OF THE INVENTION

1. Field of the Invention

This invention relates to surgical suturing and, more particularly, to an apparatus that facilitates the formation, and cinching, of a half-hitch knot, as from externally of a cavity in which a laparoscopic procedure is performed. The invention is also directed to a method of suturing utilizing the apparatus.

2. Background Art

Suturing tissue in an open body cavity is a relatively tedious and delicate procedure. This is due principally to the thinness of the suturing thread as well as its tendency to twist about its length. In a nominal suturing procedure, the thread is directed through a tissue and the ends thereof are wrapped to form a closed loop, the diameter of which can be reduced ultimately to the point that the thread is cinched at the tissue. As twisting of the thread occurs, restriction of the loop is inhibited, possibly to the point that it is impossible to cinch the knot at the body tissue, as required. Even after one half-hitch knot is formed and properly cinched, the twisting problem persists and may interfere with, or prevent, the subsequent formation of additional half-hitch knots as would "lock" the suture. When this occurs, the surgeon may be required to cut the suture and re-start the process. This process is by nature time consuming. These problems increase the overall time of the operation and contribute undesirably to hand, and overall, fatigue.

It is known to suture during laparoscopy internally of a cavity. The problems attendant the conventional open procedure described above are present. In fact, these problems are aggravated by reason of having to handle the suturing thread almost completely through the use of elongate instruments. The surgeon is required to extend at least two instruments into the operative cavity and to watch the procedure through a monitor that employs optical fibers extended into the cavity. This type of suturing process may be time consuming and frustrating to the surgeon, particularly in those instances when partially, or improperly formed sutures, must be cut and removed from the cavity.

It is also known to form a half-hitch knot on a suture from a location externally of the tissue. This method, known as extra-corporeal suturing, involves the step of directing a suture carrying needle through a cannula, through internal body tissue, and out the cannula so that the free ends of the suturing thread are accessible from externally of the cavity. The surgeon then manipulates the free ends of the suturing thread by wrapping the threads in such a manner as to define a half-hitch knot. An elongate "pusher" rod, with a bifurcated free end, is engaged with one of the free ends of the thread in the vicinity of where they are wrapped and pressed through the cannula, while at the same time holding both free thread ends projecting away from the loop. As this takes place, the loop diameter restricts to the point that it is ultimately cinched at the tissue.

This procedure is convenient from the standpoint that the half-hitch knots can be formed from externally of the body cavity. However, this introduces other complications. The problem of thread tangling persists. Further, the procedure is inherently awkward by requiring that the free ends of the suture projecting away from the loop be held taut as a pusher is pressed through the cannula to reduce the loop diameter. Thus, there are three manipulation points—the two free ends of the thread projecting away from the loop must be held and one of the threads at the wrapped portion of the loop must be pressed through the cannula. The result is that the procedure may require two sets of hands.

Further, the thread is prone to escaping from the open free end of the pusher. When this occurs, the surgeon is required to attempt to reposition the thread in the pusher end. This is a difficult and time consuming procedure that may be made impossible by twisting of the thread that occurs within the cavity. The end result of this may be that the surgeon may be required to remove the partially locked suture and re-start the procedure.

Further, since the thread is prone to twisting, the thread may bind as the loop diameter is restricted. Excessive pressure exerted by the pusher on the thread with this condition may result in thread breakage.

SUMMARY OF THE INVENTION

In one form of the invention, an instrument is provided for facilitating the formation of a knot in a flexible line having a first portion extending through a tissue/organ and first and second free ends projecting away from the first portion. The instrument has a body defining a passage through which the first and second free ends of the flexible line can be passed in a first direction to be exposed at a tying location on the body. First structure is provided on the body for supporting a suture loop defined by wrapping the first and second free ends of the flexible line around each other. Second structure is provided on the body, spaced from the first structure, for releasably holding one of the first and second free ends of the flexible line.

Using the inventive instrument, the other of the first and second free ends of the flexible line can be held and the loop contracted to cinch the tissue/organ through which the flexible line extends by directing at least one of the first and second free ends of the flexible line at the loop off of the first structure and through the body passage in a direction opposite to the first direction.

A third structure can be provided on the body spaced from the first structure for releasably holding the other of the first and second free ends of the flexible line.

It is possible with this arrangement to place the free ends of the flexible line in a state wherein they are held without the assistance of the user, whereupon the user can focus on resurfacing the loop and cinching the tissue/organ with the flexible line.

The invention further contemplates the instrument in combination with a flexible line.

The body may have a cup-shaped wall opening in the first direction and defining a space within which the first structure at least partially resides.

In one form, the body has a cylindrical sleeve defining the passage and there is structure on the body for at least partially sealing the passage.

The second structure may captively hold the one of the first and second free ends of the flexible line.

In one form, the second structure includes first and second parts defining first and second shoulders, and there is first structure cooperating between the first and second parts for selectively placing the first and second parts in a) a first relative position wherein the first and second shoulders are spaced sufficiently from each other that the one of the first and second free ends of the flexible line can be moved freely therebetween and b) a second relative position wherein the first and second shoulders captively hold the one of the first and second free ends of the flexible line therebetween.

The first and second parts may be threadably connected so that they are movable towards and away from each other by relatively rotating them.

The first structure may be in the form of a rod with structure cooperating between the rod and body for mounting the rod to the body for movement relative to the body between a) a tying position wherein the suture loop is supported on the rod and b) a release position wherein the first and second free ends of the flexible line at the loop can be directed off of the rod and through the body in a direction opposite to the first direction.

The rod may be translatable between the tying position and the release position.

The rod in the tying position may intersect the space defined by an extension of the body passage in the first direction.

The third structure may captively hold the other of the first and second free ends of the flexible line.

In one form, the passage has an axis and there are first and second elongate arms extending radially away from the axis of the passage, with the second structure being on the first arm and the third structure being on the second arm.

The length of the arms may extend angularly in relation to the axis of the passage. For example, this angle may be 45°.

In another form of the invention, an instrument is provided having a body with first structure on the body for releasably holding one of the first and second free ends of the flexible line and second structure on the body for releasably holding the other of the first and second free ends of the flexible line.

With this arrangement, a user can wrap the free ends of the flexible line around each other to define a loop and thereafter use the first and second structures to hold the free ends of the flexible line, whereupon the loop diameter can be diminished and the tissue/organ cinched with the free ends of the flexible line held by the first and second structures.

The invention further contemplates a method of forming a knot in a flexible line extending through a tissue/organ, which method includes the steps of providing a flexible line, directing a first portion of the flexible line through a tissue/organ such that first and second free ends of the flexible line project away from the first portion, providing an instrument having a body with first structure thereon for supporting a suture loop and second structure thereon for releasably holding one of the first and second free ends of the flexible line, wrapping the first and second free ends of the flexible line around each other to define a loop, supporting the loop on the first structure, holding a part of one of the first and second free ends of the flexible line on the second structure, holding a part of the other of the first and second free ends of the flexible line, engaging one of the first and second free ends of the flexible line at the loop, and urging the one of the first and second free ends of the flexible line at the loop towards the first portion of the flexible line while holding the parts of the first and second free ends of the flexible line to thereby cinch the tissue/organ.

In one form, the instrument has a third structure thereon for releasably holding a part of the other of the first and second free ends of the flexible line and the step of holding a part of one of the first and second free ends of the flexible line involves the step of holding a part of the one of the first and second free ends of the flexible line on the third structure.

The first structure on the instrument may be a repositionable rod, with the method including the step of repositioning the rod on the body to release the loop from the rod.

The invention further contemplates the step of providing a cannula, directing the cannula through a tissue into a body cavity, providing a sleeve on the instrument body, and directing the body sleeve into the cannula so that the cannula and sleeve define an uninterrupted passage through the tissue and into the body cavity.

The invention further includes the step of releasing the first and second free ends of the flexible line after cinching the tissue/organ with the flexible line, wrapping the first and second free ends of the flexible line around each other to define a second loop with a half-hitch knot, and reducing the size of the second loop progressively until the second loop cinches the tissue/organ.

The step of holding a part of the one of the first and second free ends of the flexible line may involve releasably captively holding a part of the one of the first and second free ends of the flexible line between first and second facing shoulders on the body.

DETAILED DESCRIPTION OF THE DRAWINGS

In FIGS. 1–5, an instrument, according to the present invention, is shown at 10, for facilitating the tying of a knot in a flexible line/thread that is extended through a tissue/organ 14, as to close an incision 16.

Figure 2:
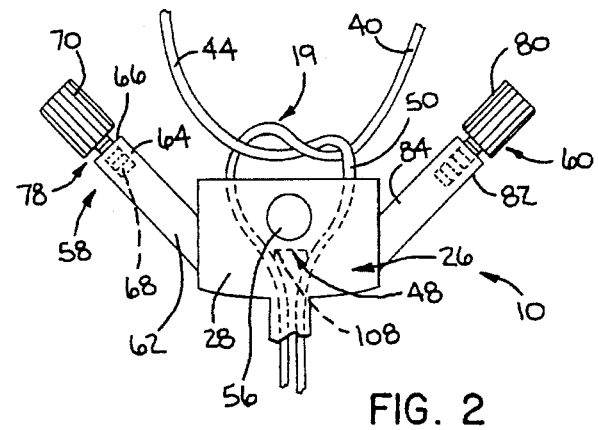
FIG. 2 is a fragmentary, side elevation view of the inventive instrument with the free ends of the flexible line wrapped around each other to define a loop using a half-hitch knot.
Figure 3:
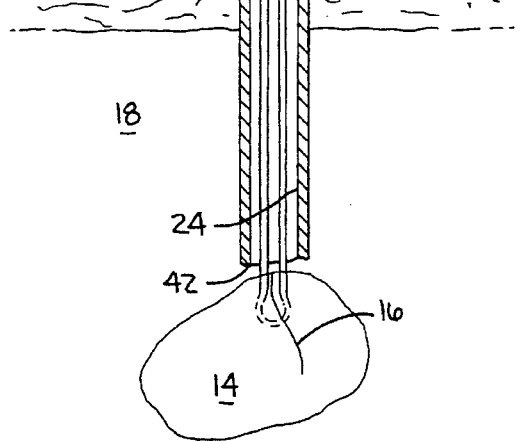
FIG. 3 is a view as in FIG. 2 with the loop supported on the instrument and the free ends thereof releasably held in place on the instrument.
Figure 4:
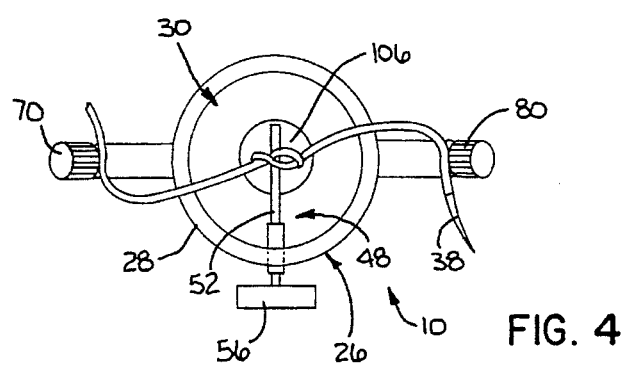
FIG. 4 is a plan view of the instrument with the thread positioned as in FIG. 3 and with a loop supporting structure in a first/tying position.
Figure 5:
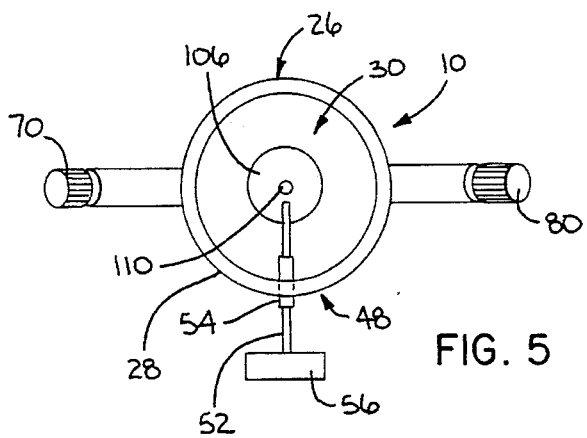
FIG. 5 is a view as in FIG. 4 with the loop supporting structure in a second/release position.
Figure 8:
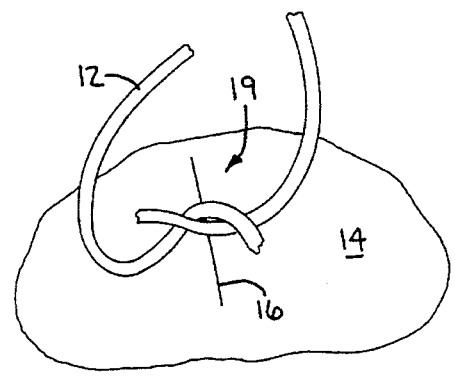
FIG. 8 is a perspective view of a tissue/organ with the above knot cinched thereagainst.
Figure 9:
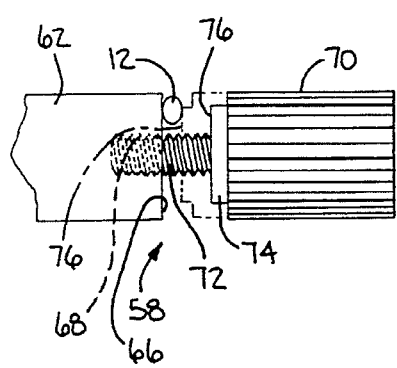
FIG. 9 is an enlarged, front elevation view of structure for releasably holding one of the free ends of the thread as the suture is formed, with the structure in a release position in solid lines and in a holding position in phantom lines.

One object of the invention is to allow formation of a half-hitch knot in the thread 12, as shown at 19 in FIGS. 2 and 8, from a location externally of a cavity 18 in which the tissue/organ 14 resides.

More particularly, the instrument 10 can be directed into a hollow, conventional cannula 20 extending through a tissue 22 bounding the cavity 18. The cannula 20 defines an internal passage 24 that communicates from the cavity 18, adjacent to the tissue/organ 14, to a point externally of the tissue 22.

The instrument 10 has a body 26 with a cup-shaped wall 28, made from Ultem, bounding a tying space 30. The body 28 has a depending, cylindrical sleeve 32 that can be projected into the cannula 20 into a fully seated position, whereupon a surface 34 at the bottom of the wall 28 abuts to the top edge 36 of the cannula 20. The sleeve 32 is preferably made from stainless steel. The sleeve 32 and cannula 20 cooperatively define a continuous, uninterrupted passageway between the tissue/organ 14 and the tying space 30.

Figure 1:
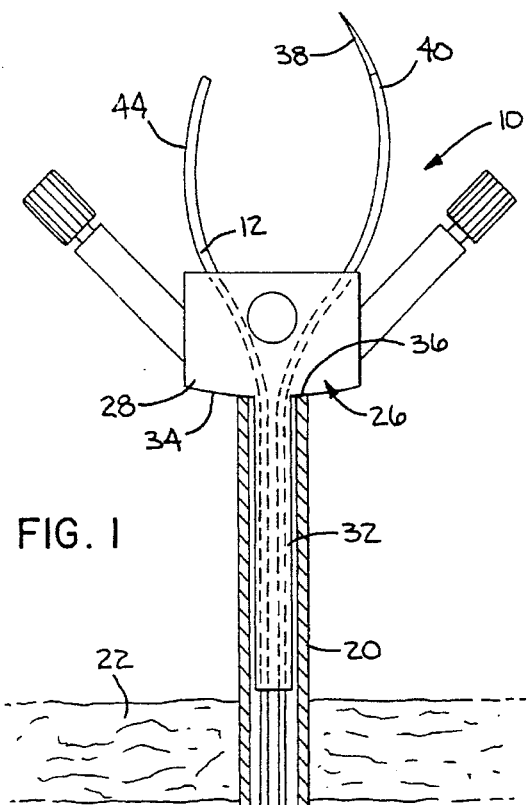
FIG. 1 is a side elevation view of an instrument for facilitating the formation of a knot in a flexible line, made according to the present invention, and with the instrument extending through a cannula and a flexible line extending through the instrument and a tissue/organ and having its free ends exposed to be tied.

To tie a suture, a needle 38 on the leading free end 40 of the thread 12 is directed by an appropriate laparoscopic instrument downwardly through the passageway defined by the sleeve 32 and cannula 20, in a first direction, outwardly through the distal free end 42 of the cannula 20 into the tissue/organ 14 on one side of the incision 16, outwardly through the tissue/organ 14 on the other side of the incision 16, and back upwardly through the passageway in the cannula 20 and sleeve 32 until the arrangement in FIG. 1 is arrived at.

Once the thread is placed as shown in FIG. 1, the leading thread end 40 and the trailing free end 44 are wrapped around each other as shown in FIG. 2 to define a half-hitch knot which results in the formation of a continuous loop 50 extending through the tissue/organ. According to the invention, means is provided at 48 for supporting the knotted end of the loop 50. The means 48 is in the form of an elongate rod 52. The rod 52 is received slidably within a sleeve 54 extending through the wall 28. With this arrangement, the rod 52 is translatable between a release position, shown in FIG. 5, and a tying position, shown in FIG. 4. In the latter position, the rod 52 projects across the passageway defined by the sleeve 32 and cannula 20, as viewed from the top of the instrument 10. An enlarged head 56 is provided on the rod 52 to facilitate its transition between the tying and release positions.

The ends 40, 44 of the thread 12 are extended around diametrically opposite sides of the rod 52 and wrapped as in FIG. 2 with the rod 52 in its tying position. The loop diameter is reduced by &awing on the thread ends 40, 44 until the loop 50 is drawn tautly against the rod 52, thereby stabilizing the loop 50.

The body has separate means at 58 and 60 for releasably holding and thereby stabilizing the thread ends 40, 44. Each of the means 58, 60 is the same, and thus description herein will be limited to the exemplary means 58, as shown in detail in FIGS. 1–5 and 9.

The means 58 is on an elongate arm 62 which extends from the body 26 angularly upwardly with respect to the length of the sleeve 32. Preferably this angle is on the order of 45°. The distal end 64 of the arm 62 has a flat shoulder 66 and a blind, threaded bore 68 therein.

A cap 70 has a stem 72 that can be threaded into the bore 68. The cap 70 has a reduced diameter portion 74 with a flat shoulder 76 that faces oppositely to the shoulder 66 on the arm 62.

The cap 70 can be trotted in one direction relative to the arm 62 to define a space 78 between the shoulders 66, 76 into which the thread 12 can be directed. By then turning the cap 70 in the opposite direction, the shoulder 76 is moved towards the shoulder 66 until the thread 12 is captively squeezed therebetween.

The means 60 includes a like cap 80, which is threaded to the distal end 82 of an elongate arm 84 projecting angularly away from the wall 28. Each of the caps 70, 80 has a knurled outer surface to facilitate rotation thereof.

With the loop 50 drawn taut against the rod 52, the thread end 44 can be drawn taut and captively placed between the cap 70 and arm 64 and the thread end 40 similarly drawn taut and placed captively between the cap 80 and arm 84. The surgeon can then with one hand stabilize the instrument 10 and with the other hand engage one of the ends 40, 44 at the knot 19 and push that thread end downwardly through the sleeve 32 and cannula 20 towards the tissue/organ 14 to thereby cinch the tissue/organ 14 at the incision 16.

Figure 6:
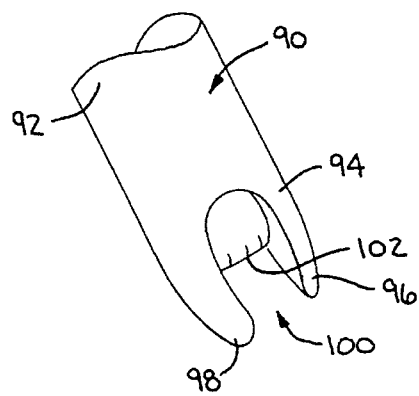
FIG. 6 is a fragmentary, perspective view of the end of a pusher rod used to engage the thread at the loop and press the thread towards the suturing area to diminish the loop size and effect cinching of the tissue/organ.
Figure 7:
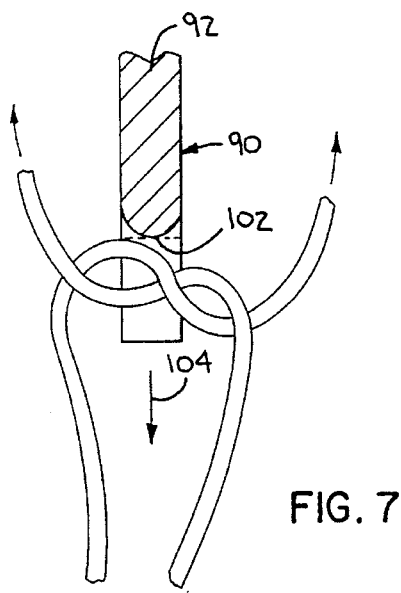
FIG. 7 is a fragmentary, cross-sectional view of the pusher rod positioned to engage the thread loop to reduce the diameter thereof.

This latter step is facilitated by the use of an elongate pusher rod, as shown at 90 in FIGS. 6 and 7. The pusher rod has an elongate body 92 with a bifurcated, distal free end 94. The free end 94 has legs 96, 98 with an entryway 100 therebetween.

The thread 12 can be directed through the entryway 100 against a rounded shoulder 102, facing lengthwise of the body 92. Continuous movement of the pusher rod 90 and thread 12, in the direction of the arrow 104, through the cannula 20 causes the loop 50 to reduce in diameter and ultimately to cinch, as shown in FIG. 8.

Since the thread ends 40, 44 remain exposed and accessible to the surgeon, the tying process can be repeated to form another knotted loop, which can then be reduced in diameter through the use of the pusher rod 90, or other suitable means.

To prevent escape of gas from the cavity 18 through the cannula 20 and sleeve 32, a seal 106 is provided. The seal 106 may take the form of an inverted, cup-shaped cap that is frictionally held on a stepped, upstanding stem 108 at the base of the tying space 30. The seal 106, which may be a rubber-type element, has an opening 110 therethrough to facilitate passage of the thread 12 during a suturing operation. With the inventive arrangement, the loop 50 slides consistently downwardly to the target area without twisting. Consequently, it can be consistently cinched and positively tightened at the appropriate site on the tissue/organ.

The instrument 10, as described above, can be re-used. It can be sterilized in an autoclave using a standard cycle.

The foregoing disclosure of specific embodiments is intended to be illustrative of the broad concepts comprehended by the invention.

I claim:

1. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

repositionable first means on the body for supporting a suture loop defined by wrapping the first and second free ends of the flexible line around each other, said first means being repositionable between a) a first position wherein the first means supports a suture loop and b) a second position wherein a suture loop supported on the first means can be released from the first means; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction.

2. The instrument for facilitating the formation of a knot in a flexible line according to claim 1 further including third means on the body spaced from the first means for releasably holding the other of the first and second free ends of the flexible line.

3. The instrument for facilitating the formation of a knot in a flexible line according to claim 2 wherein the third means comprises means for captively holding the other of the first and second free ends of the flexible line.

4. The instrument for facilitating the formation of a knot in a flexible line according to claim 1 in combination with a flexible line.

5. The instrument for facilitating the formation of a knot in a flexible line according to claim 1 wherein the second means comprises means for captively holding the one of the first and second free ends of the flexible line.

6. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

first means on the body for supporting a suture loop defined by wrapping the first and second free ends of the flexible line around each other; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction, wherein the body has a cup-shaped wall opening in the first direction and defining a space within which the first means at least partially resides.

7. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

first means on the body for supporting a suture loop defined by wrapping the first and second free ends of the flexible line around each other; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction, wherein the body has a cylindrical sleeve defining the passage and there is means on the body for at least partially sealing the passage.

8. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

first means on the body for supporting a suture loop defined by wrapping the first and second free ends of the flexible line around each other; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction, wherein the second means comprises means for captively holding the one of the first and second free ends of the flexible line, wherein the second means comprises first and second parts defining first and second shoulders and there are first means cooperating between the first and second parts for selectively placing the first and second parts in a) a first relative position wherein the first and second shoulders are spaced sufficiently from each other that the one of the first and second free ends of the flexible line can be moved freely therebetween and b) a second relative position wherein the first and second shoulders captively hold the one of the first and second free ends of the flexible line therebetween.

9. The instrument for facilitating the formation of a knot in a flexible line according to claim 8 wherein the first cooperating means comprises means for threadably engaging the first and second parts.

10. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

first means on the body for supporting a suture loop defined by wrapping the first and second free ends of the flexible line around each other; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction, wherein the first means comprises a rod and means cooperating between the rod and body for mounting the rod to the body for movement relative to the body between a) a tying position wherein the suture loop is supported on the rod and b) a release position wherein the first and second free ends of the flexible line at the loop can be directed off of the rod and through the body in a direction opposite to the first direction.

11. The instrument for facilitating the formation of a knot in a flexible line according to claim 10 wherein the rod is translatable between the tying position and the release position.

12. The instrument for facilitating the formation of a knot in a flexible line according to claim 10 wherein the rod in the tying position intersects a space defined by an extension of the body passage in the first direction.

13. An instrument for facilitating the formation of a knot in a flexible line having a first portion extending through a tissue/organ and first and second free ends projecting away from the first portion, said instrument comprising:

a body defining a passage through which the first and second free ends of the flexible line can be passed in a first direction to be exposed at a tying location on the body;

first means on the body for supporting a suture loop defined by wrapping the first and second free ends of the flexible line around each other; and second means on the body spaced from the first means for releasably holding one of the first and second free ends of the flexible line, whereby the other of the first and second free ends of the flexible line can be held and the loop contracted to cinch the tissue/organ through which the flexible line extends by directing at least one of the first and second free ends of the flexible line at the loop off of the first means and through the body passage in a direction opposite to the first direction, there further being a third means on the body spaced from the first means for releasably holding the other of the first and second free ends of the flexible line, wherein the passage has an axis, there are first and second elongate arms extending radially away from the axis of the passage, the second means is on the first arm and the third means is on the second arm.

14. The instrument for facilitating the formation of a knot in a flexible line according to claim 13 wherein the length of at least one of the arms extends at approximately a 45° angle to the axis of the passage.

15. A method of forming a knot in a flexible line extending through a tissue/organ, said method comprising the steps of:

providing a flexible line;

directing a first portion of the flexible line through a tissue/organ such that first and second free ends of the flexible line project away from the first portion;

providing an instrument having a body with a first means thereon for supporting a suture loop and a second means thereon for releasably holding one of the first and second free ends of the flexible line;

wrapping the first and second free ends of the flexible line around each other to define a loop;

supporting the loop on the first means;

holding a part of one of the first and second free ends of the flexible line on the second means;

holding a part of the other of the first and second free ends of the flexible line;

engaging one of the first and second free ends of the flexible line at the loop; and urging the one of the first and second free ends of the flexible line at the loop towards the first portion of the flexible line while holding the parts of the first and second free ends of the flexible line to thereby cinch the tissue/organ, wherein the first means on the instrument comprises a repositionable rod and including the step of repositioning the rod on the body to release the loop from the rod.

16. A method of forming a knot in a flexible line extending through a tissue/organ, said method comprising the steps of:

providing a flexible line;

directing a first portion of the flexible line through a tissue/organ such that first and second free ends of the flexible line project away from the first portion;

providing an instrument having a body with a first means thereon for supporting a suture loop and a second means thereon for releasably holding one of the first and second free ends of the flexible line;

wrapping the first and second free ends of the flexible line around each other to define a loop;

supporting the loop on the first means;

holding a part of one of the first and second free ends of the flexible line on the second means;

holding a part of the other of the first and second free ends of the flexible line;

engaging one of the first and second free ends of the flexible line at the loop; and urging the one of the first and second free ends of the flexible line at the loop towards the first portion of the flexible line while holding the parts of the first and second free ends of the flexible line to thereby cinch the tissue/organ, said method further including the steps of providing a cannula, directing the cannula through a tissue into a body cavity, providing a sleeve on the instrument body, and directing the body sleeve into the cannula so that the cannula and sleeve define an uninterrupted passage through the tissue and into the body cavity.

17. A method of forming a knot in a flexible line extending through a tissue/organ, said method comprising the steps of:

providing a flexible line;

directing a first portion of the flexible line through a tissue/organ such that first and second free ends of the flexible line project away from the first portion;

providing an instrument having a body with a first means thereon for supporting a suture loop and a second means thereon for releasably holding one of the first and second free ends of the flexible line;

wrapping the first and second free ends of the flexible line around each other to define a loop;

supporting the loop on the first means;

holding a part of one of the first and second free ends of the flexible line on the second means;

holding a part of the other of the first and second free ends of the flexible line;

engaging one of the first and second free ends of the flexible line at the loop; and urging the one of the first and second free ends of the flexible line at the loop towards the first portion of the flexible line while holding the parts of the first and second free ends of the flexible line to thereby cinch the tissue/organ, said method further including the steps of releasing the first and second free ends of the flexible line after cinching the tissue/organ with the flexible line and wrapping the first and second free ends of the flexible line around each other to define a second loop and reducing the size of the second loop progressively until the second loop cinches the tissue/organ.

* * * * *